Figure 1:
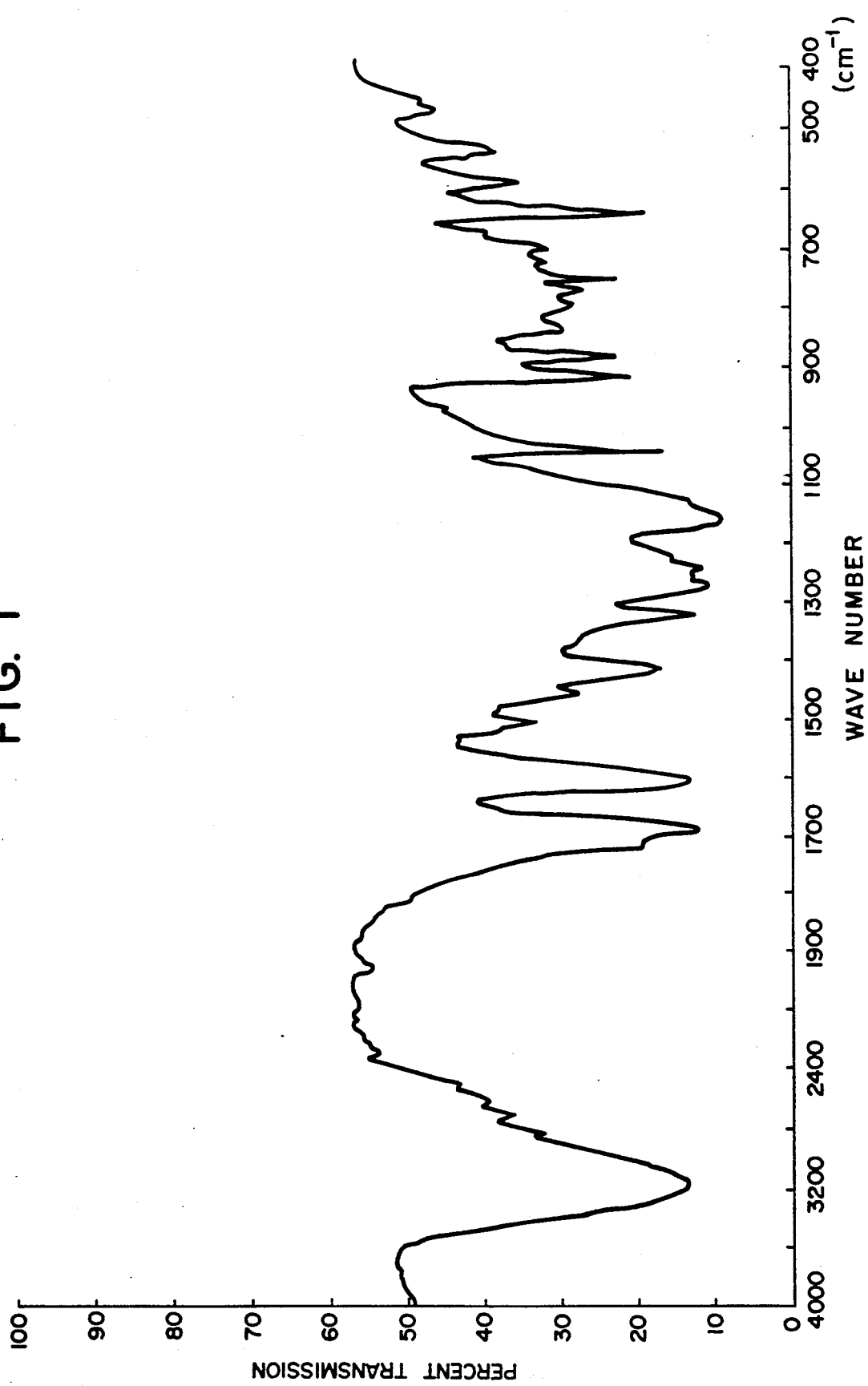

United States Patent [19]

Suzuki

[11] Patent Number: 5,183,934

[45] Date of Patent: Feb. 2, 1993

[54] 2-TRIFLUOROMETHYL-4-HYDROXYBENZOIC ACID

[75] Inventor: Yoshiichi Suzuki, Tokyo, Japan

[73] Assignee: Showa Shell Sekiyu Kabushiki Kaisha, Tokyo, Japan

[21] Appl. No.: 859,961

[22] Filed: Mar. 30, 1992

Related U.S. Application Data

[63] Continuation of Ser. No. 599,456, Oct. 18, 1990, abandoned.

[51] Int. Cl.$^5$ ............................................. C07C 51/15
[52] U.S. Cl. ...................................... 562/423; 560/65
[58] Field of Search ........................... 562/423; 560/65

[56] References Cited

U.S. PATENT DOCUMENTS 3,790,528  2/1974  Tesaki et al. ...................... 260/47 C

FOREIGN PATENT DOCUMENTS 134959  3/1985  European Pat. Off. .

OTHER PUBLICATIONS

Ekisho Polimaa (Liquid Crystal Polymer) pp. 13, 14, 20 and 25 published by CMC (Jun. 5, 1987).
Hauptschein et al., Trifluoromethyl Derivatives of Hydroxybenzoic Acids and Related Compounds, Journal of the American Chemical Society, 1051 (Feb. 20, 1954).

Primary Examiner—Paul J. Killos
Attorney, Agent, or Firm—Cushman, Darby & Cushman

[57] ABSTRACT

Disclosed is a novel compound 2-trifluoromethyl-4-hydroxybenzoic acid represented by the formula:

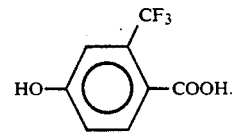

3 Claims, 1 Drawing Sheet

2-TRIFLUOROMETHYL-4-HYDROXYBENZOIC ACID

This is a continuation of application Ser. No. 07/599,456, filed Oct. 18, 1990 now abandoned.

The present invention relates to novel 2-trifluoromethyl-4-hydroxybenzoic acid.

Various studies have been made on trifluoromethyl group-containing compounds and the following compounds have been reported as compounds close to the compound of the present invention:

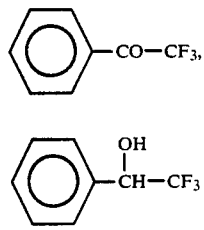

The present invention relates to 2-trifluoromethyl-4-hydroxybenzoic acid represented by the following formula:

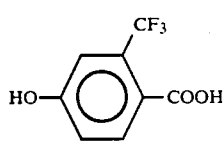

The present 2-trifluoromethyl-4-hydroxybenzoic acid (hereinafter referred to as "present compound") is a novel compound which has not been reported in any literatures.

The present compound is prepared through the following synthesis route.

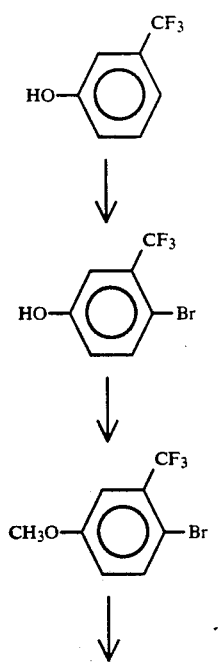

(Compound I)

(Compound II)

(Compound III)

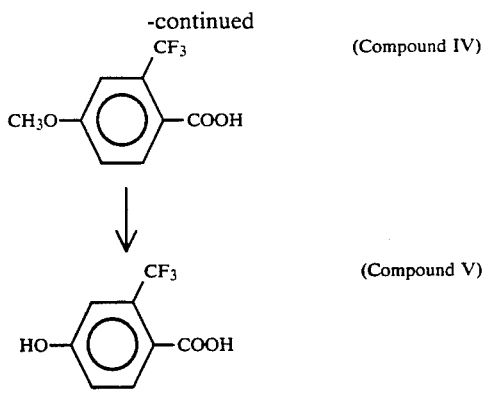

(Compound IV)

(Compound V)

The present compound is used as raw materials for condensation polymers such as polyesters; organic functional materials; liquid crystals; physiologically active substances; and intermediates for pharmaceutical and agricultural chemicals mentioned below.

The present compound is especially useful as a modifier for engineering plastics obtained by the process shown by the following reaction formula:

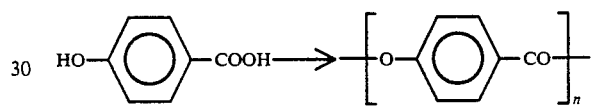

Polyester obtained by the above reaction formula have excellent performances as engineering plastics, but faults such as high melting temperature and poor processability. The processability is improved by using the present compound as a comonomer in order to modify the polyesters into the form of random copolymers or block copolymers. It is also possible to prepare polyesters represented by the following formula by condensing only the present compound.

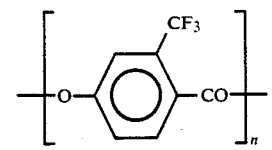

As raw materials for liquid crystals, when a bulky substituent such as the $CF_3$ group is present at the ortho-position in respect to the carboxyl group, free rotation of the C=O group is inhibited due to steric hindrance on the basis of asymmetric carbon site and phenyl ring, whereby a structure suitable for spontaneous polarization is provided.

As pharmaceuticals, compounds containing a trifluoromethyl group have been reported for nonsteroidal anti-inflammatory drugs, central nervous system agonists and antibiotics. The present compound rich in functional groups has a wide variety of uses as intermediates for introduction of the trifluoromethyl group.

FIG. 1 is an infrared spectrum of the present compound.

EXAMPLE

1. Preparation of 3-trifluoromethyl-4-bromophenol (Compound II)

3-Trifluoromethylphenol (compound I) (5.0 g) was dissolved in carbon disulfide (3.0 ml) and then to the solution was added a solution of bromine (5.0 g) in carbon disulfide (2.0 ml) over a period of about 15 minutes at 25° C. or less, followed by allowing the reaction to proceed for 2 hours at 25° C. The resulting reaction mixture was added to water (10 ml) and then subjected to repeated extraction with methylene chloride. The methylene chloride layer was washed with aqueous sodium hydrogen-carbonate solution and then with water and dehydration-dried by adding anhydrous sodium sulfate. The solvent was removed by distillation under reduced pressure to obtain 3-trifluoromethyl-4-bromophenol (compound II, 4.4 g).

2. Preparation of 3-trifluoromethyl-4-bromo-1-methoxy-benzene (compound III)

A solution prepared by dissolving 3-trifluoromethyl-4-bromo-1-phenol (4.4 g) in dehydrated dimethylformamide (20 ml) was added dropwise to a solution prepared by suspending 60% sodium hydride (0.86 g) in dehydrated dimethylformamide (10 ml) over a period of about 30 minutes at 25° C. or lower. Then, the mixture was stirred at room temperature for 30 minutes and then, methyl iodide (3.1 g) was slowly added thereto at 30° C. or lower and reaction was allowed to proceed at room temperature for 1 hour. Unreacted 60% sodium hydride was decomposed by conventional method and the reaction mixture was added to water (60 ml) and extracted with ethyl acetate and ethyl acetate layer was sufficiently washed with water and dehydrated by adding anhydrous sodium sulfate thereto. The solvent was removed by distillation under reduced pressure and the residue was purified by distillation to obtain 3-trifluoromethyl-4-bromo-1-methoxybenzene (compound III, 4.4 g).

3. Preparation of 2-trifluoromethyl-4-methoxybenzoic acid (compound IV)

Dry tetrahydrofuran (10 ml) was added to 3-trifluoromethyl-4-bromo-1-methoxybenzene (compound III) (4.4 g) and metallic magnesium (0.41 g) and thereto was further added a catalytic amount of iodine, followed by refluxing for 1.5 hours with stirring. After the temperature was returned to room temperature, to the mixture was slowly added dropwise a solution prepared by adding dry ice (30 g) to dry tetrahydrofuran (10 ml) at −40° C. or lower. The temperature was returned to room temperature and then the reaction was allowed to proceed for further 2 hours. Then, the reaction mixture was added to 1N hydrochloric acid (50 ml) to stop the reaction and repeatedly extracted with ethyl acetate. The ethyl acetate layer was sufficiently washed with water and dried by adding anhydrous sodium sulfate. The solvent was removed by distillation under reduced pressure and then, the resulting solid was recrystallized from methylene chloride to obtain 2-trifluoromethyl-4-methoxybenzoic acid (compound IV, 1.5 g).

4. Preparation of 2-trifluoromethyl-4-hydroxybenzoic acid (compound V)

A solution prepared by dissolving 2-trifluromethyl-4-methoxybenzoic acid (compound IV) (1.0 g) in methylene chloride (10 ml) was slowly added dropwise to a solution prepared by dissolving boron tribromide (2.5 g) in methylene chloride (10 ml) at 30° C. or lower with stirring, followed by stirring for further 20 minutes.

This solution was added to ice water (50 g) and then repeatedly extracted with ethyl ether. The ethyl ether layer was washed with water and dried by adding anhydrous sodium sulfate and the solvent was distilled off to obtain a crude product. This was recrystallized from toluene to obtain 2-trifluoromethyl-4-hydroxybenzoic acid (compound V, 0.5 g).

Infrared spectrum of the present compound (compound V) is shown in FIG. 1.

The present compound is useful not only as raw materials for polymer materials such as polyesters and polyester amides, but also as organic functional materials, liquid crystals and intermediates for pharmaceutical or agricultural chemicals.

What is claimed is:

1. A process for preparing 2-trifluoromethyl-4-hydroxybenzoic acid comprising:

reacting a compound represented by the formula (I):

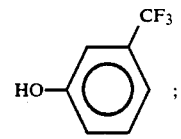

with bromine in a solvent whereby a compound represented by the formula (II) is obtained:

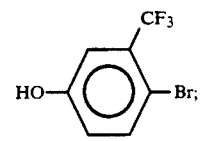

reacting a compound of formula (II) with methyl iodide at room temperature whereby a compound represented by the formula (III) is obtained:

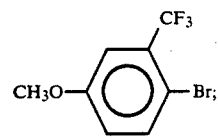

reacting a compound represented by the formula (III) with magnesium and carbon dioxide to prepare the compound represented by the formula (IV)

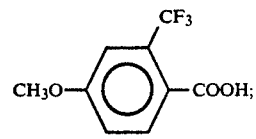

and
reacting the compound having the formula (IV) with boron tribromide.

2. A process for preparing 2-trifluoromethyl-4-hydroxybenzoic acid wherein the compound represented by the formula:

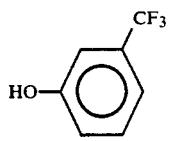 (I)

is reacted with more than the molar equivalent of bromine in a solvent to prepare the compound represented by the formula:

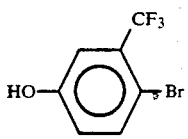 (II)

and compound II is reacted with more than the molar equivalent of methyl iodide at room temperature to prepare the compound represented by the formula:

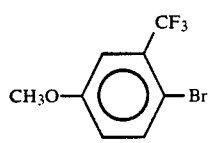 (III)

and compound III is reacted with an equal mole of magnesium and $CO_2$ to prepare the compound represented by the formula:

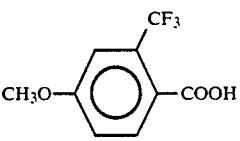 (IV)

and compound IV is reacted with boron tribromide.

3. A polyester represented by the formula

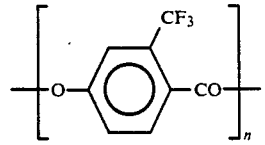

which is prepared by condensation of 2-trifluoromethyl-4-hydroxybenzoic acid

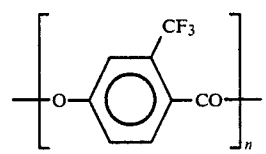

* * * * *